United States Patent
Wetzig et al.

(10) Patent No.: US 9,360,465 B2
(45) Date of Patent: Jun. 7, 2016

(54) LEAK DETECTOR

(75) Inventors: Daniel Wetzig, Köln (DE); Scott Dalton, Farmington, NY (US); Daniel Hoffmann, Irwin, PA (US); Walwyn Jackson, Jr., Syracuse, NY (US)

(73) Assignee: Inficon GmbH (DE)

( * ) Notice: Subject to any disclaimer, the term of this patent is extended or adjusted under 35 U.S.C. 154(b) by 439 days.

(21) Appl. No.: 13/820,320

(22) PCT Filed: Sep. 1, 2011

(86) PCT No.: PCT/EP2011/065110
§ 371 (c)(1),
(2), (4) Date: Apr. 9, 2013

(87) PCT Pub. No.: WO2012/028685
PCT Pub. Date: Mar. 8, 2012

(65) Prior Publication Data
US 2013/0213114 A1    Aug. 22, 2013

(30) Foreign Application Priority Data

Sep. 3, 2010 (DE) .......................... 10 2010 044 222
Oct. 20, 2010 (DE) .......................... 10 2010 048 982

(51) Int. Cl.
*G01M 3/04* (2006.01)
*G01N 33/00* (2006.01)
(Continued)

(52) U.S. Cl.
CPC ........... *G01N 33/0009* (2013.01); *G01M 3/002* (2013.01); *G01M 3/205* (2013.01); *G01N 25/20* (2013.01); *G01N 33/0032* (2013.01)

(58) Field of Classification Search
CPC ........................................................ G01M 3/04
USPC ........ 73/40, 40.7, 23.42, 25.01, 25.03, 25.05, 73/31.05; 340/605
See application file for complete search history.

(56) References Cited

U.S. PATENT DOCUMENTS

| | | |
|---|---|---|
| 3,020,746 A | 2/1962 | Minter |
| 3,786,675 A | 1/1974 | Delatorre et al. |

(Continued)

FOREIGN PATENT DOCUMENTS

| | | |
|---|---|---|
| CN | 1397798 A | 2/2003 |
| DE | 19735250 A1 | 2/1999 |

(Continued)

OTHER PUBLICATIONS

International Search Report for Application No. PCT/EP2011/065110 dated Nov. 16, 2011.

*Primary Examiner* — Hezron E Williams
*Assistant Examiner* — Hoang Nguyen
(74) *Attorney, Agent, or Firm* — Lerner, David, Littenberg, Krumholz & Mentlik, LLP

(57) ABSTRACT

The invention relates to a leak detector comprising a first sensor for detecting a gas component (helium) in a gas taken in. Because the sensor is susceptible to saturation or contamination, a second sensor is provided. The sensor is a thermal conductivity sensor. The thermal conductivity sensor has a lower detection sensitivity, yet, at a high concentration of the gas component, it does not risk being contaminated. The two sensors together allow for a large detection range, from extremely sensitive measurements to instances with high concentrations of the gas components as those which can occur with gross leaks.

20 Claims, 3 Drawing Sheets

(51) Int. Cl.
*G01M 3/00* (2006.01)
*G01M 3/20* (2006.01)
*G01N 25/20* (2006.01)

(56) References Cited

U.S. PATENT DOCUMENTS

| | | | |
|---|---|---|---|
| 6,415,650 B1 * | 7/2002 | Bohm | G01M 3/202 340/605 |
| 7,156,976 B2 | 1/2007 | Bley | |
| 7,266,991 B2 * | 9/2007 | Bley | G01M 3/205 73/23.2 |
| 7,717,681 B2 | 5/2010 | Bohm et al. | |
| 7,980,117 B2 | 7/2011 | Wetzig et al. | |
| 8,171,773 B2 * | 5/2012 | Wetzig | G01M 3/202 73/23.42 |
| 2003/0159929 A1 | 8/2003 | Werner | |
| 2004/0237631 A1 * | 12/2004 | Cohen | F02M 21/0206 73/40.7 |
| 2009/0193876 A1 * | 8/2009 | Wetrzig | G01M 3/205 73/40.7 |

FOREIGN PATENT DOCUMENTS

| | | |
|---|---|---|
| DE | 19813432 A1 | 9/1999 |
| DE | 10031882 A1 | 1/2002 |
| DE | 10246051 A1 | 4/2004 |
| DE | 102005021909 A1 | 11/2006 |
| DE | 102005047856 | 4/2007 |
| DE | 102006047856 A1 | 4/2008 |
| DE | 102008013455 A1 | 9/2009 |
| EP | 2101163 A2 | 9/2009 |
| JP | 08068711 | 3/1996 |
| JP | H09501237 A | 2/1997 |
| JP | 9292302 A | 11/1997 |
| JP | H10213516 A | 8/1998 |
| JP | H11241971 A | 9/1999 |
| JP | 2004502935 A | 1/2004 |
| WO | 95004921 A1 | 2/1995 |
| WO | 2009033978 A1 | 3/2009 |

\* cited by examiner

LEAK DETECTOR

CROSS REFERENCE TO RELATED APPLICATIONS

The present application is a national phase entry under 35 U.S.C. §371 of International Application No. PCT/EP2011/065110, filed on Sep. 1, 2011, which claims priority from German Patent Application No. 10 2010 048 982.4 filed Oct. 20, 2010 and German Patent Application No. 10 2010 044 222.4 filed Sep. 3, 2010, all of which are incorporated herein by reference.

BACKGROUND OF THE INVENTION

1. Field of the Invention

The invention refers to a leak detector for detecting at least one gas component in an aspirated gas.

2. Description of the Related Art

For a leak test using helium as the tracer gas, commercial apparatus generally detect the presence of helium by means of a mass spectrometer whose operation requires the generation of a high vacuum. Another detection method uses a membrane selectively permeable to helium, the membrane closing off a cavity in which a pressure sensor is located. Inside the cavity, a pressure is built that corresponds to the partial pressure of helium in the surrounding atmosphere. The membrane usually needs heating. Such a sensor is referred to as a partial pressure sensor in Wise Technology. It is manufactured by INFICON GmbH. Leak detectors with Wise Technology are described in DE 10 2005 021 909 A1 and in DE 10 2005 047 856 A1. Such sensors in the form of mass spectrometers or partial pressure sensors have a high sensitivity, but are susceptible to excessive concentrations of the tracer gas. The detection of helium by means of Wise Technology is limited to a partial pressure of 0.5 mbar. With gross leaks, the sensor must be protected against high concentrations. After a gross contamination, the device is blind for many seconds so that a user cannot continue the leak test. In particular, it is not possible to localize a gross leak site. When the sniffer probe reaches the vicinity of the gross leak, the system switches the sensor to the blind mode for protection. In a similar manner other sensor systems are susceptible to contamination or saturation. Also when a saturation limit is reached, concentration measurements are no longer possible.

Another sensor of the saturable gas-selective sensor type is the mass spectrometer. The mass spectrometer has a very high sensitivity and gas selectivity, but its operation requires a high vacuum, i.e. a very low value of the total pressure at its measuring input. If the total pressure rises above the allowable limit value, the mass spectrometer reaches the saturation range.

BRIEF SUMMARY OF THE INVENTION

It is an object of the invention to develop a leak detector of high sensitivity such that the measuring range is widened towards higher concentrations and higher total pressures, respectively.

A first variant of the leak detector according to the invention is defined in claim 1.

According to the invention, a first sensor of the saturable gas-selective sensor type is provided. In addition, a second sensor of the thermal conductivity sensor type is provided. The first sensor serves to measure low concentrations and the second sensor takes over the measurement at higher concentrations at which the first sensor is no longer functional.

Leak detectors including a thermal conductivity sensor are known. Examples for such sensors are described in U.S. Pat. No. 3,020,746, U.S. Pat. No. 3,786,675 and JP 09292302 A. The sensors have a temperature-dependant resistor included in a measuring bridge and arranged in a gas or a gas flow. The gas flow or the gas dissipates heat from the resistor. The higher the density of the gas is, the greater the heat dissipation from the resistor. Generally, the heating power is measured that is necessary to maintain a constant resistor temperature. The magnitude of the thermal conductivity of the resistor is indicated thereby. When the gas flowing is air including helium, the density of the overall gas decreases as the helium portion increases. Thereby, also the thermal conductivity decreases. Thermal conductivity sensors have a low gas selectivity. However, they are not dependant on saturation or contamination levels and function even at high concentrations of a gas component in an ambient gas. However, the measuring sensitivity is limited.

The definition that the first sensor is a sensor of the saturable gas-selective sensor type should be understood such that the sensor does not provide a useful quantitative measuring result above a certain concentration or a certain partial pressure of the gas component. This includes a case of contamination. Contamination occurs with high concentration values. After a gross contamination, the detector system is blind for many seconds so that the user cannot continue the leak test. In particular it is not possible to localize a gross leak site. When the sniffer probe reaches the vicinity of the gross leak, the system switches the sensor to a blind mode for protection. Among the sensors of the saturable gas-selective sensor type are the following: mass spectrometers, a wise-sensor, metal-hydride-based sensors for the detection of $H_2$, metal-oxide-based for the detection of $H_2$ (for the analysis of refrigerants or alcohol), sensors with dispersive or non-dispersive absorption.

Since the second sensor, being a thermal conductivity sensor, is not susceptible to excessive concentration values, it may be permanently active. With low concentrations, both sensor types are active, while the first sensor is switched to a blind mode when concentrations are elevated. Switching to the blind mode may be controlled both as a function of measured values of the first sensor and measured values of the second sensor.

Realizing the blind state of the first sensor can be achieved in various ways. One possibility is to cut off the gas flow to the first sensor. Another possibility is to switch the first sensor to a deactivated mode. With a wise sensor this is achieved by interrupting the heating current passing through the gas-selective membrane so that the membrane cools down and becomes less permeable.

Among other applications, the invention is useful in sniffer leak detectors where gas is aspirated into a handheld sniffer probe. The second sensor may be arranged at the sniffer probe or in a base apparatus with which the sniffer probe is connected via a flexible conduit.

Useful thermal conductivity sensors are, for example, the sensor AWM 2300 by Hamamatsu or the sensor TCS208F3 from the company Gerhard Wagner.

Using the leak detector of the present invention, it is also possible to detect refrigerants as they are used in air condition systems or refrigerators. Refrigerants have a lower conductivity than air and can therefore be differentiated from helium or hydrogen by the sign of the signal of a thermal conductivity sensor, which sign is the opposite of that of air.

A second variant of the leak detector according to the invention is defined in claim 7. Here, a switching from the first sensor to the second sensor is controlled as a function of the total pressure. Such a leak detector is useful in connection with a first sensor that is total-pressure-sensitive. Here, the second sensor covers the range above a critical total pressure, while the first sensor is used for fine measurement. The second sensor may additionally be configured such that it simultaneously measures the total pressure. In this case, the second sensor can cause the switching of the first sensor to the blind mode. As an alternative, it is also possible to provide a total pressure gauge that is independent of both sensors and controls the same.

It is also possible to operate with both sensors at the same time, with the quantity measurement being effected by means of the thermal conductivity sensor and the quality measurement (evaluation of the gas type) is effected by means of a partial pressure sensor.

BRIEF DESCRIPTION OF THE DRAWINGS

The following is a detailed description of embodiments of the invention made with reference to the drawings.

In the Figures.

DETAILED DESCRIPTION

Figure 1:
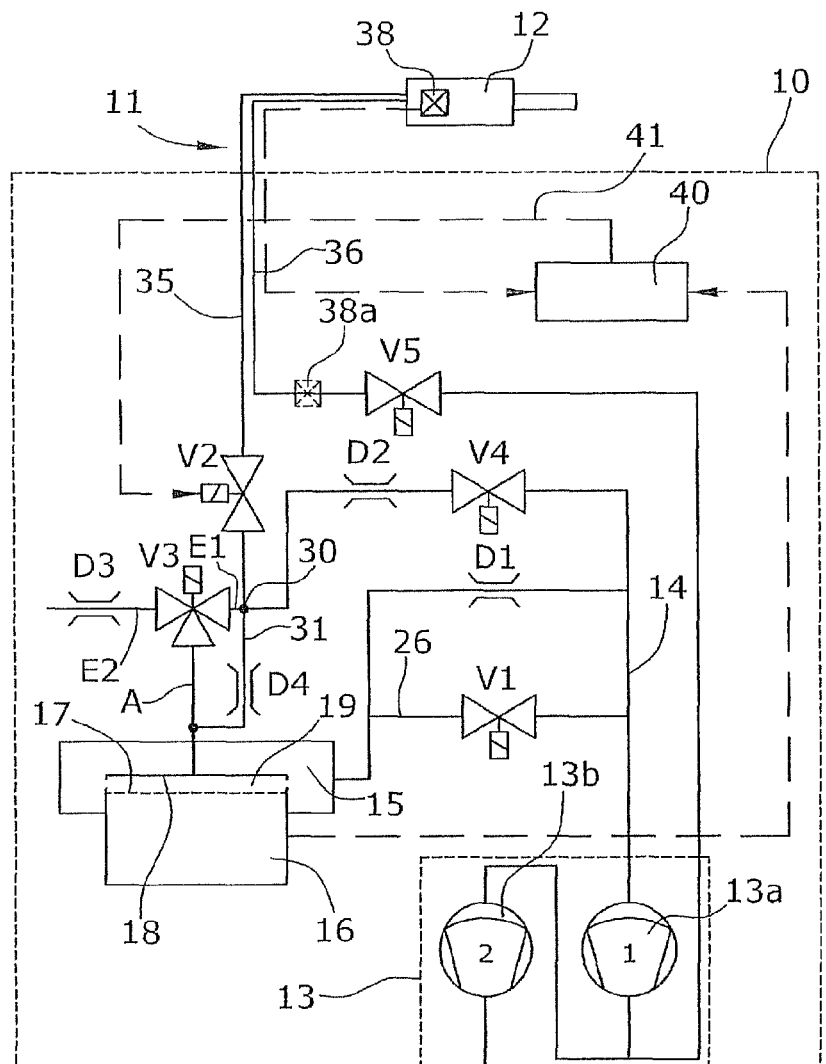
FIG. 1 is a schematic illustration of a sniffer leak detector according to a first variant of the invention.

The sniffer leak detector of FIG. 1 is provided with a base apparatus 10 connected with a sniffer probe 12 via a valve V2. The sniffer probe 12 may be guided by hand in order to check the object under test for leaks from which gas escapes.

The base apparatus 10 comprises a vacuum pump 13 which, in the present example, is a two-stage pump with the pump stages 13a and 13b that are configured as membrane pumps. The vacuum pump generates a final pressure of about 3 mbar.

A vacuum conduit 14 leads from the vacuum pump 13 to the suction chamber 15. The suction chamber 15 is formed upstream of the tracer gas sensor 16. The walls of the suction chamber 15 adjoin the housing of the tracer gas sensor 16. The sensor surface 17 of the tracer gas sensor 16 is enclosed by the suction chamber 15. Within the suction chamber 15, a gas guiding plate 18 is arranged facing the sensor surface 17 with a distance therebetween and being arrange in parallel with the same. The sniffer conduit 11 opens into the gas guiding chamber 19. The same is provided with lateral openings 20 in opposite ends, through which gas can enter the suction chamber 15. The gas guiding chamber 19 effects a distribution of the gas in front of the sensor surface 17.

The tracer gas sensor 16 is configured in the same manner as the sensor described in DE 100 31 882 A1. The sensor surface 17 is formed by a membrane selectively permeable to helium and adapted to be heated electrically or by heat radiation. For the rest, the tracer gas sensor 16 includes a Penning pressure sensor or another pressure sensor generating an electric signal that indicates the pressure in the housing closed off by a quartz membrane. From this pressure, the signal for the detected quantity of tracer gas is derived.

The vacuum conduit 14 includes a first throttle D1 between the vacuum pump 13 and the suction chamber 15, which throttle determines the suction power for the normal mode of operation. The first throttle D1 is bridged by means of a bypass conduit 26 that includes a valve V1.

A throttle D2 is provided in an air inlet conduit. The valve V3 connects either the inlet E1 or the inlet E2 with the outlet A. The inlet E1 is connected with the first flow divider 30 which is connected with the inlet of the tracer gas sensor 16 via a conduit 31. The conduit 31 includes a throttle D4.

Another path extends from the flow divider 30 via a throttle D2 and a valve V4 to the vacuum conduit 14. The throttles D2 and D4 are adjusted to each other such that the flow through D2 is much larger than the flow through D4. The flow through D2 is at least 10 times the flow through D4 and in particular at least 50 times. Preferably, the flow through D2 is about one hundred times the flow through D4.

The sniffer conduit 11 leading from the sniffer probe 12 to the base apparatus 10 includes a measuring conduit 35 connecting the sniffer probe with the valve V2 and an intake conduit 36 connected with the inlet of the vacuum pump 13 via a valve V5. The intake conduit 36 has a much greater suction capacity than the measuring conduit 35. For example, the flow rate of the gas taken in through the measuring conduit is 300 sccm, whereas the flow arte through the intake conduit 36 is 2700 sccm. The intake conduit 36 serves to increase the distance sensitivity of the sniffer leak detector by taking in much more gas as in the case of the measuring conduit. The measuring sensitivity is increased by deactivating the intake conduit.

According to the invention, a second sensor 38 is provided in addition to the first sensor 16 which is configured as a Wise Technology sensor, the second sensor being a thermal conductivity sensor. The second sensor 38 is preferably arranged in the sniffer probe 12 and in particular in the intake conduit 36 thereof. It may also be situated in the base apparatus 10 at a position 38a. In any case, it is advantageous to arrange the second sensor at a site where a high total pressure prevails, since this is where the partial pressure of the gas component of interest is the highest and thus the detection limit is most favorable. Another possibility for the positioning of the second sensor exists at the outlet of the vacuum pump 13. Here, it would be unfavorable, however that the signal from the second sensor would occur later in time than the signal from the first sensor. Preferably, the signal from the thermal conductivity sensor should be available earlier than the signal from the first sensor.

The signals from the first sensor 16 and from the second sensor 38 are supplied to a control means 40 switching the first sensor 16 to the blind mode via a control line 41, when the first sensor or the second sensor measures a concentration above a limit value. Thereby, it is prevented that the first sensor becomes saturated or exceeds the contamination limit, respectively.

Figure 2:
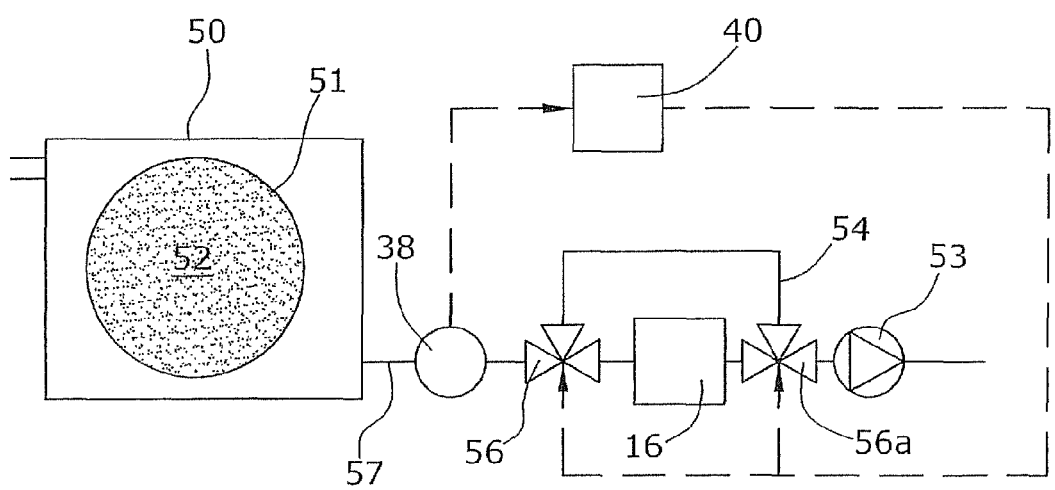
FIG. 2 is a schematic illustration of a leak detector with a test chamber.

The embodiment shown in FIG. 2 is a leak detector which is provided with a vacuum-tight test chamber 50 in which a test object 51 is placed. The test object 51 is filled with a tracer gas 52. The test chamber 50 is evacuated so that in case of a leak in the test object 51, tracer gas leaks from the test object. A vacuum pump 53 is connected to the test chamber 50 via an intake conduit 57. The intake conduit 57 includes a first sensor 16 and a second sensor 38. The first sensor may be a Wise Technology sensor, for example, while the second sensor is a thermal conductivity sensor. In the flow path of the gas taken in, the second sensor 38 is arranged upstream of the first sensor 16. The first sensor 16 is bridged by a bypass conduit 54 that can be opened and closed by the valves 56, 56a.

The valve 56 is controlled by a control device as a function of the signal from the second sensor 38. If the tracer gas concentration measured by the second sensor exceeds a limit value, the valves 56 and 56a are switched over such that the first sensor 16 is bridged by means of the bypass conduit 54. Thereby, the first sensor is protected from contamination.

Figure 3:
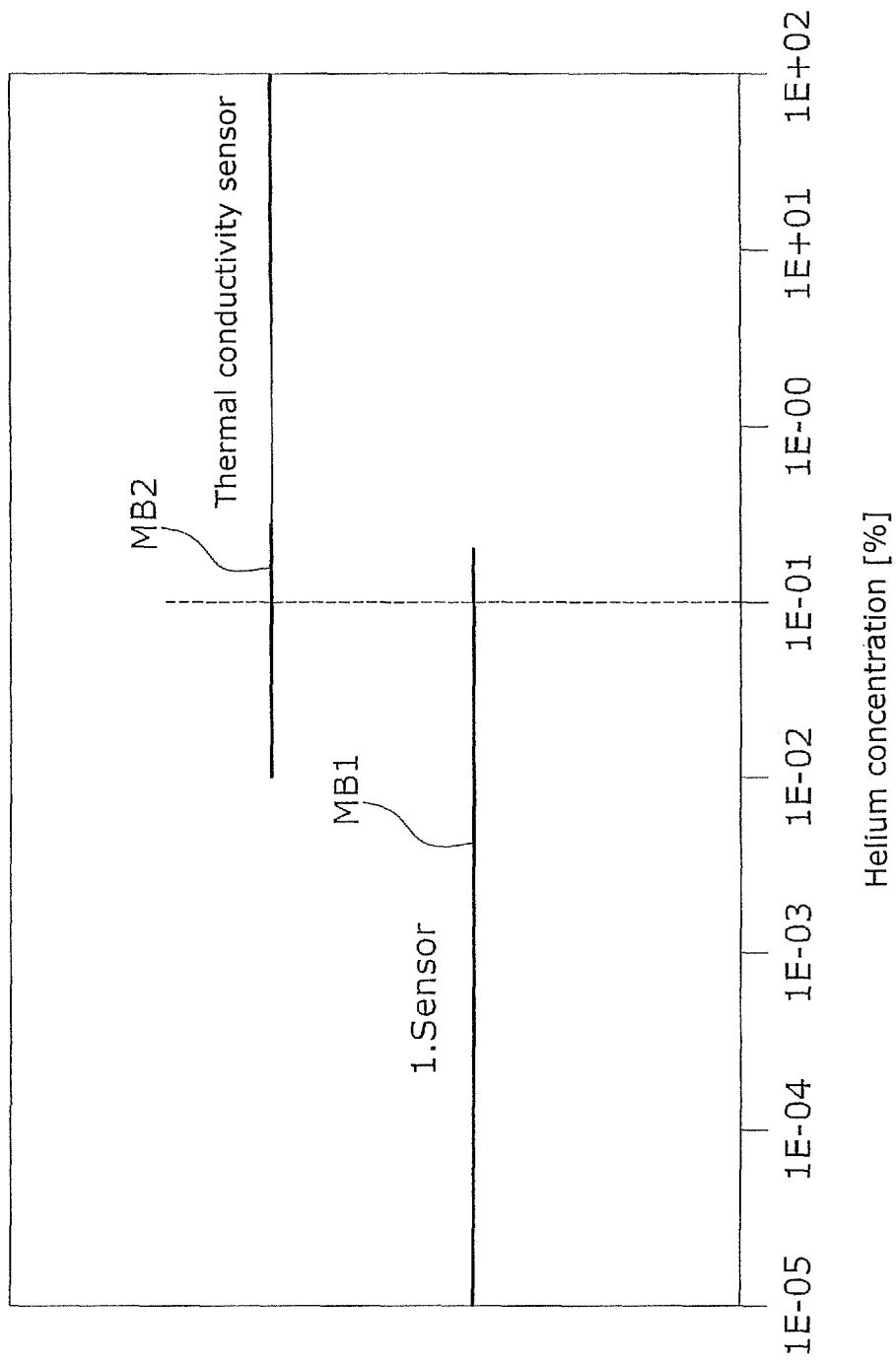
FIG. 3 is a diagram showing the measuring ranges of the two sensor types.

FIG. 3 illustrates an example for the measurement ranges of the first sensor and the second sensor using the gas component helium as an example. The helium concentration is plotted along the abscissa. It can be seen that the measurement range MB1 of the first sensor ranges from less than 1E-05% (=$10^{-4}$ mbar) to slightly above 1E-01% (=1 mbar), whereas the measurement range MB2 of the thermal conductivity sensor covers the entire range above 1E-02%. Thus, both sensors complement each other.

Figure 4:
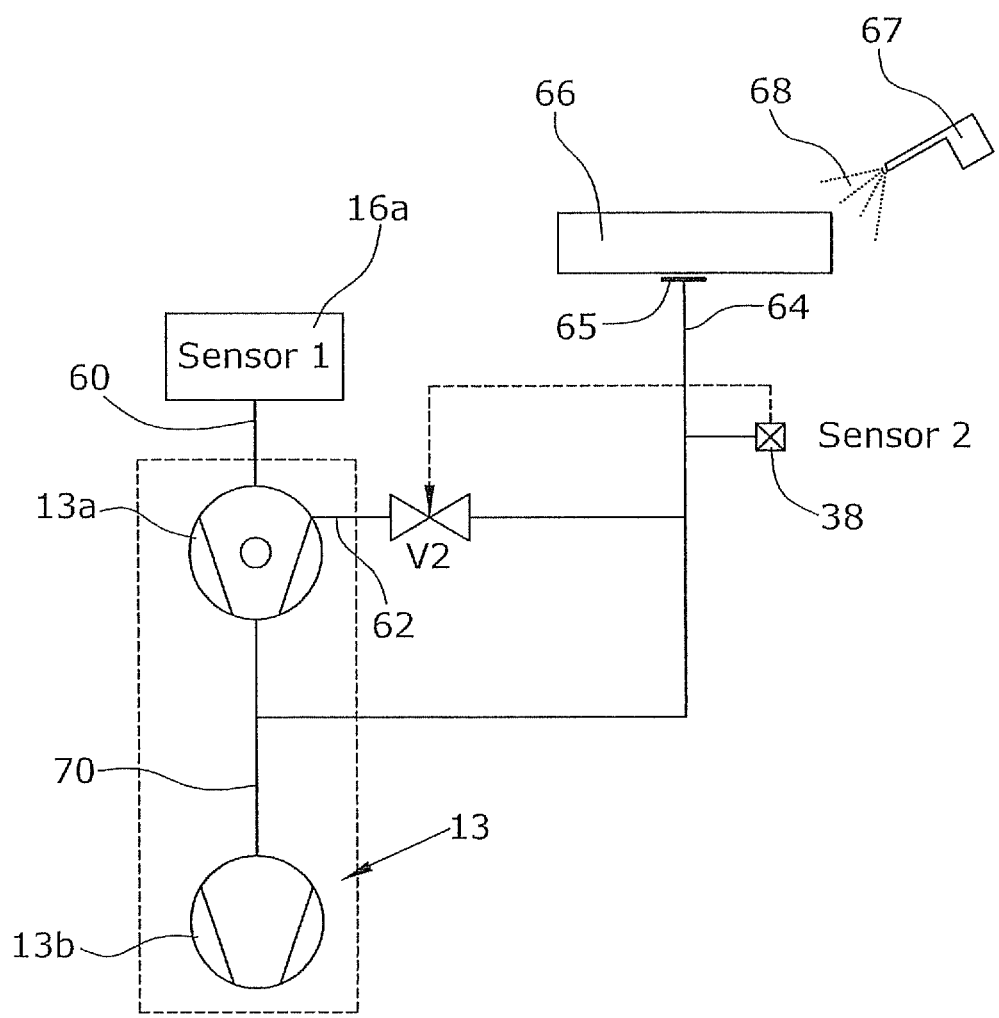
FIG. 4 is a schematic illustration of an embodiment according to a second variant of the invention.

FIG. 4 illustrates an embodiment according to the second variant of the invention, in which a first sensor 16a is provided whose function depends on the total pressure at its measuring inlet 60, e.g. a mass spectrometer. The measuring inlet 60 is connected to a vacuum pump 13 including, arranged in succession, a high vacuum pump 13a, for example a turbomolecular pump, and a rough vacuum pump 13b. An intake 62 of the high vacuum pump 13a is connected with an inlet conduit 64 via a valve V2, the conduit comprising a connection 65 for connecting a test object 66. The test object 66 is a hollow body to be tested for tightness. In the present embodiment, an atmosphere of a tracer gas 68 is created outside the test object using a spraying apparatus 67. The tracer gas can be identified by the two sensors included in the leak detector. When tracer gas is identified, the test object 66 has a leak through which tracer gas 68 has entered.

The inlet conduit 64 is further connected to a connecting conduit 70 that connects the two vacuum pumps 13a and 13b.

A valve V2 is connected between the intake 62 and the inlet conduit 64, the valve being controlled in dependence on the total pressure and being switched to a closing mode when the total pressure rises above a limit value. When the valve V2 is closed, the first sensor 16a is separated from the test object 66 so that the sensor is switched to the blind mode.

The second sensor 38 is connected to the inlet conduit 64, the sensor being a thermal conductivity sensor. This thermal conductivity sensor is designed such that, at higher pressures, it operates independent of the total pressure. With lower total pressures prevailing at the measuring inlet 60 both sensor types are active, whereas at higher total pressures, the first sensor 16a is switched to the blind mode by closing the valve V2. In the present embodiment, the total pressure is measured at the inlet conduit 64 using the second sensor 38. Alternatively, it could also be effected at the measuring inlet 60 of the first sensor. It is also possible to use a separate apparatus for the measurement of the total pressure.

The invention claimed is:

1. A leak detector with a vacuum pump device through which gas is taken in, and a first sensor for detecting at least one gas component in the gas taken in, the first sensor is a saturable gas-selective sensor,
   wherein a second sensor is a thermal conductivity sensor and is provided to detect the thermal conductivity of the gas taken in, and a signal-receiving control device for switching the first sensor to a blind mode when the first and/or the second sensor detects a concentration of the at least one gas component above a limit value, the first sensor covering a range of low concentrations of the at least one gas component and the second sensor covering a range of high concentrations of the at least one gas component.

2. The leak detector of claim 1, wherein a valve is arranged upstream of the first sensor in a gas flow of gas taken in, said valve being switched by the signal-receiving control device to a closed state in order to realize the blind mode.

3. The leak detector of claim 1, wherein the first sensor comprises a heatable, selectively gas-permeable membrane, and heating the membrane is deactivated in order to realize the blind mode.

4. The leak detector of claim 1, wherein a sniffer probe is provided for taking in gas from the atmosphere, and the first sensor is included in a measuring conduit and the second sensor is included in an intake conduit, the intake conduit leading directly from the sniffer probe to the vacuum pump device and carrying a higher flow rate than the measuring conduit, so as to increase distance sensitivity.

5. The leak detector of claim 1, wherein the second sensor is arranged at a position where a constant total pressure prevails that approximates atmospheric pressure.

6. The leak detector of claim 1, further comprising a bypass conduit including valves controlled by the signal-receiving control device.

7. The leak detector of claim 5, wherein the second sensor is arranged in an intake conduit or at an air outlet of the leak detector.

8. A leak detector with a vacuum pump device through which gas is taken in, and a first sensor for detecting at least one gas component in the gas taken in, the first sensor is a saturable gas-selective sensor,
   wherein a second sensor is a thermal conductivity sensor and is provided to detect the thermal conductivity of the gas taken in, and a signal-receiving switch for switching the first sensor to a blind mode when the first and/or the second sensor detects a concentration of the at least one gas component above a limit value, the first sensor covering a range of low concentrations of the at least one gas component and the second sensor covering a range of high concentrations of the at least one gas component.

9. The leak detector of claim 8, wherein a valve is arranged upstream of the first sensor in a gas flow of gas taken in, said valve being switched by the signal-receiving switch to a closed state in order to realize the blind mode.

10. The leak detector of claim 8, wherein the first sensor comprises a heatable, selectively gas-permeable membrane, and heating the membrane is deactivated in order to realize the blind mode.

11. The leak detector of claim 8, wherein a sniffer probe is provided for taking in gas from the atmosphere, and the first sensor is included in a measuring conduit and the second sensor is included in an intake conduit, the intake conduit leading directly from the sniffer probe to the vacuum pump device and carrying a higher flow rate than the measuring conduit, so as to increase distance sensitivity.

12. The leak detector of claim 8, wherein the second sensor is arranged at a position where a constant total pressure prevails that approximates atmospheric pressure.

13. The leak detector of claim 8, further comprising a bypass conduit including valves controlled by the signal-receiving switch.

14. The leak detector of claim 12, wherein the second sensor is arranged in an intake conduit or at an air outlet of the leak detector.

15. A leak detector with a vacuum pump device through which gas is taken in, and a first sensor for detecting at least one gas component in the gas taken in, the first sensor is a saturable gas-selective sensor,
   wherein a second sensor is a thermal conductivity sensor and is provided to detect the thermal conductivity of the gas taken in, and a switching valve for switching the first sensor to a blind mode when the first and/or the second sensor detects a concentration of the at least one gas component above a limit value, the first sensor covering a range of low concentrations of the at least one gas component and the second sensor covering a range of high concentrations of the at least one gas component.

16. The leak detector of claim 15, wherein the switching valve is arranged upstream of the first sensor in a gas flow of gas taken in, said valve switching to a closed state in order to realize the blind mode.

17. The leak detector of claim 15, wherein a sniffer probe is provided for taking in gas from the atmosphere, and the first sensor is included in a measuring conduit and the second sensor is included in an intake conduit, the intake conduit leading directly from the sniffer probe to the vacuum pump device and carrying a higher flow rate than the measuring conduit, so as to increase distance sensitivity.

18. The leak detector of claim 15, wherein the second sensor is arranged at a position where a constant total pressure prevails that approximates atmospheric pressure.

19. The leak detector of claim 15, further comprising a bypass conduit including the switching valve.

20. The leak detector of claim 18, wherein the second sensor is arranged in an intake conduit or at an air outlet of the leak detector.

* * * * *